United States Patent [19]

Preller

[11] Patent Number: 5,263,970
[45] Date of Patent: Nov. 23, 1993

[54] SURGICAL DRESSING FOR CLOSING A WOUND

[76] Inventor: Siegfried F. Preller, 7 Seder Street, Vanderbijlpark, Transvaal Province, South Africa

[21] Appl. No.: 737,618

[22] Filed: Jul. 30, 1991

[30] Foreign Application Priority Data

Aug. 10, 1990 [ZA] South Africa .................. 90/6348

[51] Int. Cl.[5] ................ A61F 13/00; A61F 15/00; A61F 17/00
[52] U.S. Cl. ................... 606/216; 606/214; 606/215; 602/58
[58] Field of Search ............ 606/214, 215, 216; 602/58; 128/888

[56] References Cited

U.S. PATENT DOCUMENTS

| | | | |
|---|---|---|---|
| 2,818,865 | 1/1958 | Jacoby | 606/216 |
| 4,038,989 | 8/1977 | Romero-Sierro et al. | 606/216 |
| 4,815,468 | 3/1989 | Annand | 606/216 |

FOREIGN PATENT DOCUMENTS

| | | | |
|---|---|---|---|
| 0346012 | 9/1919 | Fed. Rep. of Germany | 606/215 |
| 0551713 | 6/1932 | Fed. Rep. of Germany | 606/215 |
| 0692496 | 7/1965 | Italy | 606/216 |
| 2083753 | 3/1982 | United Kingdom | 606/216 |

*Primary Examiner*—Paul Prebilic
*Attorney, Agent, or Firm*—Sprung Horn Kramer & Woods

[57] ABSTRACT

A surgical dressing 10 for closing a wound includes a pair of locating members 12, 14, the locating members 12, 14, in use, being placed on opposed sides of the wound. A manipulating means 22 interconnects the locating members 12, 14, the manipulating means 22 and the locating members 12, 14 being a one piece article and the manipulating means 22 being operable to draw the locating members 12, 14 towards each other to close the wound.

7 Claims, 3 Drawing Sheets

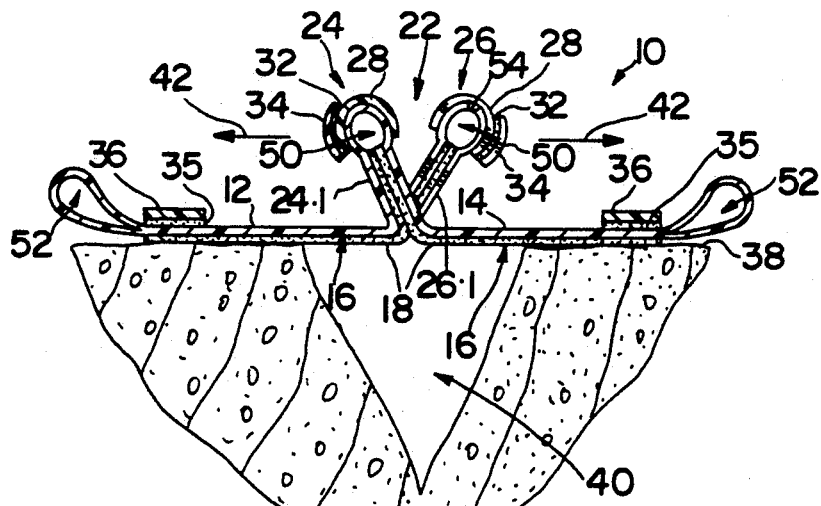

SURGICAL DRESSING FOR CLOSING A WOUND

FIELD OF THE INVENTION

THIS INVENTION relates to a surgical dressing for closing a wound.

SUMMARY OF THE INVENTION

According to the invention, there is provided a surgical dressing for closing a wound, the dressing including a pair of locating members, the locating members, in use, being placed on opposed sides of the wound; and a manipulating means interconnecting the locating members, the manipulating means and the locating members being a one-piece article and the manipulating means being operable to draw the locating members towards each other to close the wound.

Each locating member may comprise a strip of material, an operatively lower surface of each strip carrying an adhesive coating for adhesive bonding with skin surrounding the wound. Each coating may be covered with a backing sheet which is removed for use.

The manipulating means may comprise two sets of limb-like or elongate members, the limb-like members being formed as integral extensions of facing sides of the locating members.

The limb-like members of one set may be interposed between the limb-like members of the other set such that the sets extend from the locating members away from each other.

Each limb-like member may be formed by adhesively bonding corresponding extensions of the facing sides of the locating members together.

Free ends of the limb-like members in each set may be interconnected by a tab portion. A surface of each tab portion facing towards the locating members may carry an adhesive coating thereon for securing the tab portion either on the locating members or directly on the skin after the wound has been closed.

Each tab portion may have zones of weakness defined therein for effecting separation of the free ends of the limb-like members of each set from one another.

In another embodiment of the invention, each tab portion defines an opening extending therethrough, transversely to the limb-like members. Each locating member may also have an opening defined therein which extends transversely to the limb-like members.

If desired, at least a portion of an upper surface of each strip may also carry an adhesive coating for bonding between the tab portions and the strips.

The invention is now described by way of example with reference to the accompanying diagrammatic drawings.

BRIEF DESCRIPTION OF THE DRAWINGS

In the drawings,

FIGS. 6 to 8 show schematic side views of the dressing, in accordance with a further embodiment of the invention, in use.

DETAILED DESCRIPTION OF THE DRAWINGS

Figure 1:
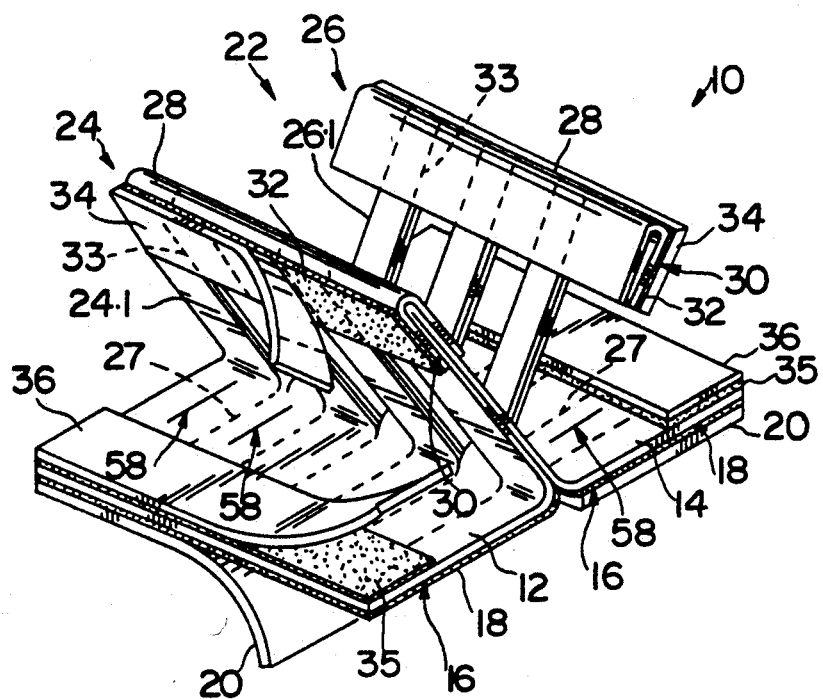
FIG. 1 shows a three dimensional view of a surgical dressing, in accordance with the invention, for closing a wound.

Referring to the drawings, a surgical dressing, in accordance with the invention, for closing a wound is illustrated and is designated generally by the reference numeral 10. The dressing 10 comprises two locating members each of which is in the form of a strip 12, 14 of a suitable material such as, for example, a synthetic plastics material. Preferably, the material is at least semi-transparent for rendering the wound visible through the dressing 10.

An operatively lower surface 16 of each strip 12, 14 carries a coating 18 of adhesive material for bonding with the skin of a person. The coating 18 of adhesive material of each strip 12, 14 is covered by a backing sheet 20 which is removed for use.

A manipulating means 22 interconnects the strips 12, 14. The manipulating means 22 comprises two sets of limb-like or elongate elements 24, 26. The set 24 has a plurality of spaced limbs 24.1. Similarly, the set 26 has a plurality of spaced limbs 26.1. The limbs 26.1 of the element 26 extend between the limbs 24.1 of the element 24.

The limbs 24.1 and 26.1 of the sets 24 and 26, respectively, are formed by elongate extensions of facing sides of the strips 12, 14 and are integral with the facing sides of the strips 12, 14. Each limb 24.1, 26.1 is formed by mating and adhesively bonding corresponding extensions of the strips 12, 14. Prior to use, the limbs 24.1 and 26.1 are interconnected along lines or zones of weakness 27 which can be ruptured to separate the limbs 24.1 and 26.1.

Free ends of the limbs 24.1, 26.1 of each set 24, 26 carry a tab portion 28. An operatively lower surface 30 of each tab portion 28 carries a coating 32 of an adhesive material. The coatings 32 are covered by backing sheets 34. Zones or lines of weakness 33 extend transversely through the tab portions 28 for enabling individual limbs 24.1, 26.1 to be separated from one another for facilitating manipulation of individual limbs 24.1 and 26.1 when required.

As illustrated, an operatively upper surface of each strip 12, 14 carries a transversely extending coating 35 of adhesive material, the coatings 35 being covered by backing sheets 36 which are removed for use.

Figure 3:
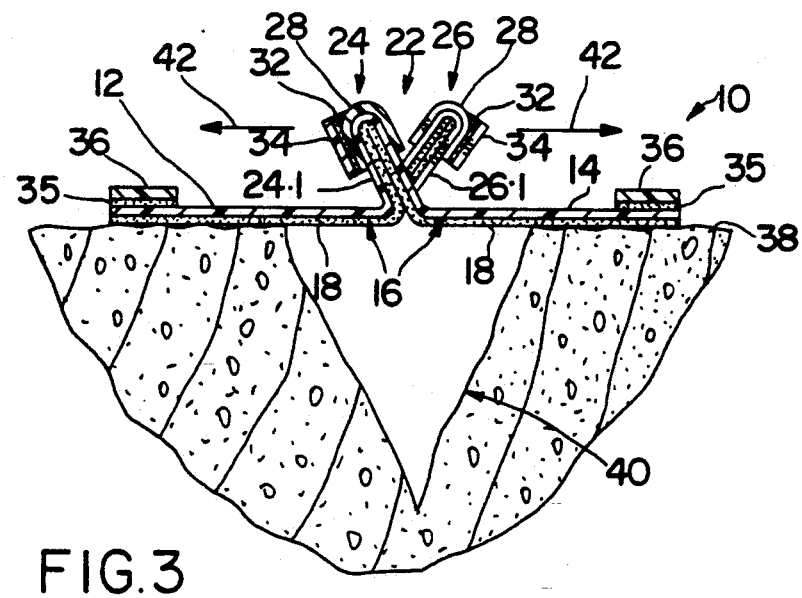
FIGS. 3 to 5 show schematic side views of the dressing, in use.
Figure 4:
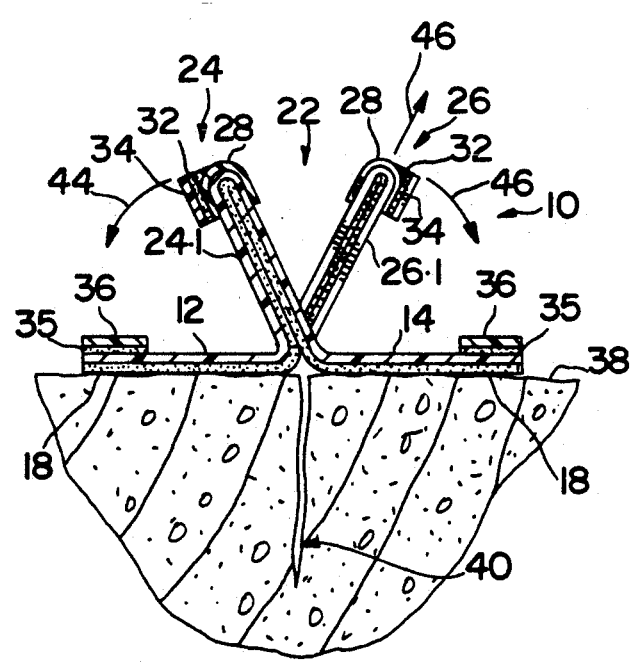
Figure 5:
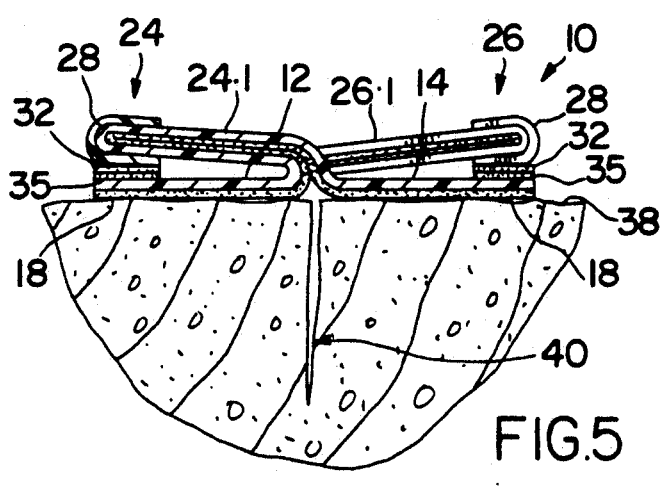

In use, and as illustrated more clearly in FIGS. 3 to 5 of the drawings, the backing sheets 20 covering the coatings 18 of the strips 12 and 14 are removed and the strips 12 and 14 are placed on a person's skin 38 on opposed sides of a wound 40 in the skin 38 so that the strips 12 and 14 bond adhesively with the skin 38.

The limbs 24.1 and 26.1 of the sets 24 and 26 are then drawn in opposite directions as illustrated by arrows 42 to draw the strips 12 and 14 towards each other to close the wound 40 as illustrated in FIG. 4 of the drawings. The backing sheets 34 covering the coatings 32 of the tab portions 28 of the sets 24, 26 are then removed. The backing sheets 36 covering the adhesive coatings 35 on the strips 12, 14 are also removed and the tab portion 28 of the set 24 is folded onto the strip 12 in the direction of arrow 44. Similarly, the tab portion 28 of the set 26 is folded onto the strip 14 in the direction of arrow 44 so that the limbs 24.1 and 26.1 adopt the position shown in FIG. 5 of the drawings.

Figure 2:
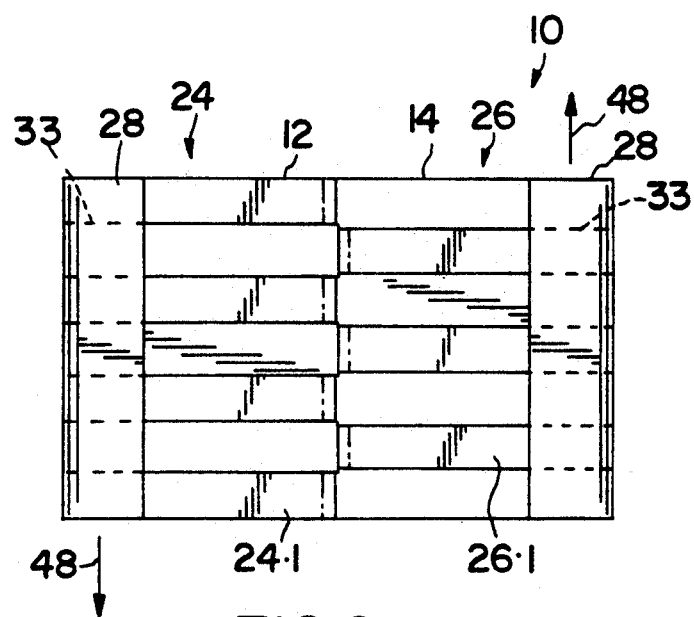
FIG. 2 shows a plan view of the dressing.

It will be appreciated that other ranges of manipulation of the wound 40 can be achieved using the dressing 10. Thus, in addition to opening or closing the wound by manipulation of the sets 24, 26 in the direction of arrows 42, "up and down" movement of the skin 38 surrounding the wound 40 can be effected. This is achieved by pulling one of the limbs 24.1 or 26.1 (which has been separated from its adjacent limb along the lines of weakness 33) away from the skin 38 in the direction of arrow 46 (FIG. 4) whilst pressing the limbs 26.1 or 24.1 on opposite sides of the individual limb 24.1 or 26.1 onto the skin 38. Further, sideways manipulation of the wound 40 can be achieved by pulling the tab-like elements 24 and 26 in opposite directions as illustrated by arrows 48 in FIG. 2 of the drawings.

Referring to the embodiment of the invention shown in FIGS. 6 to 8 of the drawings, like reference numerals refer to like parts, unless otherwise specified.

In this embodiment of the invention, each set 24, 26 of the manipulating means 22 has a loop 50 defined in free ends of the limbs 24.1, 26.1. Similarly, outer edges of the strips 12, 14 have loops 52 defined therein.

The loops 50 and 52 are used in the case of larger wounds where special dressings or bandages (not shown) are used by being inserted through the loops 50 to support and retain the dressing 10 around the body or limb having the wound. This is especially advantageous for larger abdominal type wounds where the bandage would be placed around the torso of the person. The loops 52 in the strips 12, 14 are used in a similar fashion.

In certain cases, the loops 50 may be cut, as illustrated at 54, and the extensions 26.1.1 or 26.1.2 (or 24.1.1 and 24.1.2, as the case may be) are separated down to the wound in order further to facilitate manipulation of the skin 38 around the wound 40 in an up/down direction to achieve mating of the edges of the skin on opposite side of the wound 40. Thereafter, the layers 26.1.1 and 26.1.2 or 24.1.1 and 24.1.2 are adhered to each other again prior to further manipulation of the sets 24, 26 in the direction of arrows 44.

Still further, prior to the manipulation of the dressing 10 in the direction of arrows 44, cuts may be made, as illustrated at 56 in FIG. 7 of the drawings, after the wound 40 has been closed, but prior to manipulation of the sets 24, 26 in the direction of arrows 44. By making these cuts 56 in the layers 24.1.2 or 26.1.2 in the limbs 24.1 or 26.1, the sideways manipulation of the dressing 10 in the direction of arrows 48 (FIG. 2) is facilitated.

Finally, marks 58 (FIG. 1) are provided on the upper surface of the strips 12, 14 to locate the dressing 10 with respect to corresponding marks (not shown) on the skin 38, for example, in the case of an operation.

Thus, by means of the invention a dressing 10 is provided which can be used for small wounds 40 not serious enough to warrant stitching or for larger wounds where the skin 38 can be closed without stitches, provided such larger wounds have the necessary subcuticular stitches. Still further, by the vast range of manipulations which can be achieved using the dressing 10, other wounds such as abrasions or areas of skin loss, where a certain degree of compression of the wound is needed, can be treated with the dressing 10.

I claim:

1. A surgical dressing for closing a wound, the dressing including
a pair of locating members oriented along a longitudinal axis, the locating members, in use, being placed on opposed sides of the wound, each locating member comprising a strip of material, an operatively lower surface of each strip carrying an adhesive coating for adhesive bonding with skin surrounding the wound; and a manipulating means interconnecting the locating members, the manipulating means and the locating members being a one-piece article and the manipulating means comprising two sets of elongate members, the elongate members being formed as integral extensions of facing sides of the locating members, free ends of the elongate members in each set being interconnected to transversely spaced free ends by a tab portion, each tab portion having zones of weakness defined therein for effecting separating of the free ends of the elongate members of each set from one another, the manipulating means being operable to draw the locating members towards each other to close the wound.

2. The dressing as claimed in claim 1 in which each coating is covered with a backing sheet which is removed for use.

3. The dressing as claimed in claim 1 in which the elongate members of one set are interposed between the elongate members of the other set such that the sets extend from the locating members away from each other.

4. The dressing as claimed in claim 1 in which each elongate member is formed by adhesively bonding corresponding extensions of the facing sides of the locating members together.

5. The dressing as claimed in claim 1 in which a surface of each tab portion facing towards the locating members carries an adhesive coating thereon for securing the tab portions either on the locating members or directly on the skin after the wound has been closed.

6. The dressing as claimed in claim 1 in which each tab portion includes a loop which defines an opening extending therethrough, transversely to the elongate members.

7. The dressing as claimed in claim 6 in which each locating member also includes a loop which defines an opening extending therethrough, transversely to the elongate members.

* * * * *